(12) United States Patent
Holderby

(10) Patent No.: US 12,042,376 B2
(45) Date of Patent: Jul. 23, 2024

(54) SPRING-LOADED PLUNGER FOR ADVANCE OF INTRAOCULAR LENS

(71) Applicant: Alcon Inc., Fribourg (CH)

(72) Inventor: Victoria Holderby, Arlington, TX (US)

(73) Assignee: Alcon Inc., Fribourg (CH)

( * ) Notice: Subject to any disclaimer, the term of this patent is extended or adjusted under 35 U.S.C. 154(b) by 837 days.

(21) Appl. No.: 16/941,350

(22) Filed: Jul. 28, 2020

(65) Prior Publication Data

US 2021/0038369 A1 Feb. 11, 2021

Related U.S. Application Data

(60) Provisional application No. 62/883,284, filed on Aug. 6, 2019.

(51) Int. Cl.
*A61F 2/16* (2006.01)
*A61F 2/48* (2006.01)

(52) U.S. Cl.
CPC ............ *A61F 2/167* (2013.01); *A61F 2/1678* (2013.01); *A61F 2002/1683* (2013.01); *A61F 2002/16905* (2015.04); *A61F 2/482* (2021.08); *A61F 2/484* (2021.08); *A61F 2250/006* (2013.01)

(58) Field of Classification Search
CPC ....... A61F 2/1662; A61F 2/167; A61F 2/1678
See application file for complete search history.

(56) References Cited

U.S. PATENT DOCUMENTS

| | | | |
|---|---|---|---|
| 8,336,752 B2 | 12/2012 | Viola | |
| 9,364,316 B1 | 6/2016 | Kahook et al. | |
| 2014/0257317 A1* | 9/2014 | Safabash | A61F 2/1662 606/107 |
| 2017/0319332 A1 | 11/2017 | Kahook et al. | |
| 2020/0197158 A1* | 6/2020 | Liu | A61F 2/1678 |

* cited by examiner

*Primary Examiner* — William H Matthews
(74) *Attorney, Agent, or Firm* — Patterson + Sheridan, LLP

(57) ABSTRACT

Systems, methods, and devices for inserting an intraocular lens (IOL) assembly into an eye may be provided. An apparatus for delivery of a lens component into an eye, including: a housing; a nozzle operatively coupled to the housing; a plunger at least partially and moveably disposed within the housing for driving the lens component; and a spring that applies a biasing force to the plunger.

15 Claims, 7 Drawing Sheets

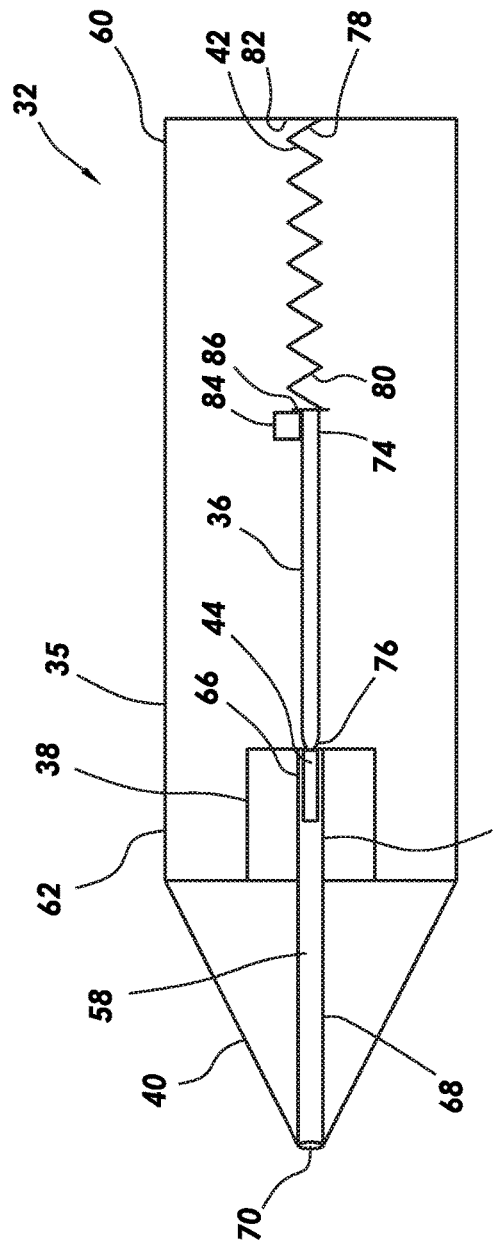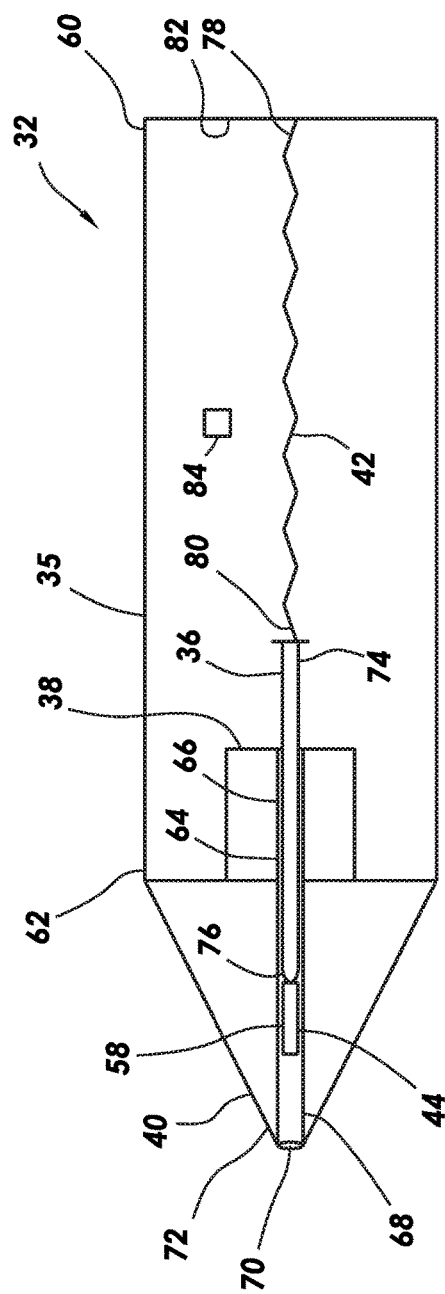
FIG. 6A
FIG. 6B

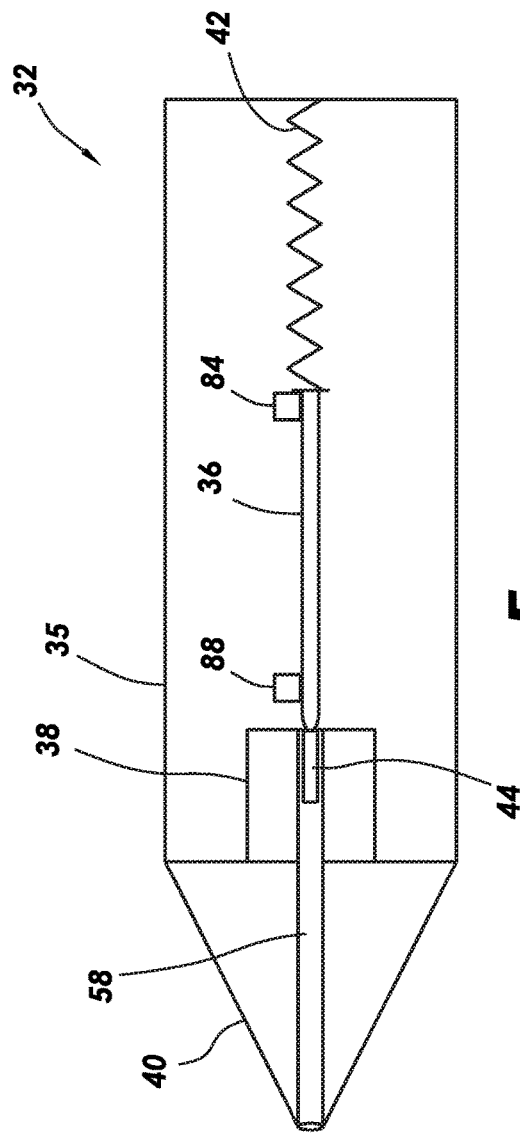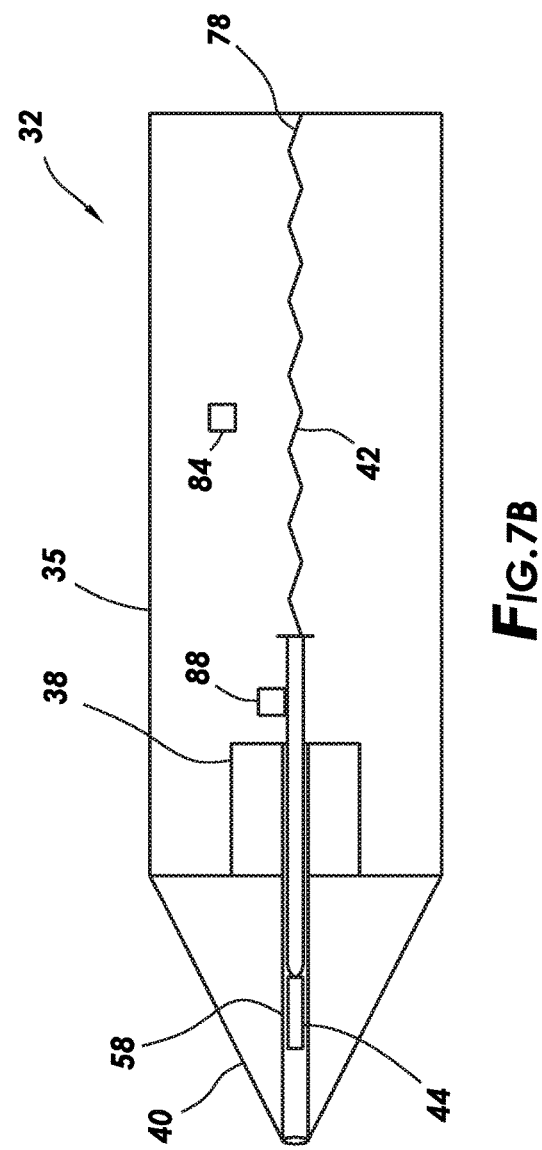

SPRING-LOADED PLUNGER FOR ADVANCE OF INTRAOCULAR LENS

CROSS-REFERENCE TO RELATED APPLICATIONS

This application claims priority to and benefit of U.S. Provisional Patent Application No. 62/883,284, filed Aug. 6, 2019, the entire contents of which are incorporated by reference herein in their entirety.

TECHNICAL FIELD

The present disclosure may generally relate to eye surgery and, more particularly, example embodiments may generally relate to systems, methods, and devices for inserting an intraocular lens (IOL) that employ a plunger that is spring loaded.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate lens holder may be loaded into the insertion tool. The plunger may engage the IOL to advance the IOL from the lens holder, through the nozzle, and into the eye. The lens holder (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the lens holder to a well position. The IOL may be pre-folded or may be folded when advanced from the storage position to the dwell position. At the dwell position, forward advancement of the IOL may be halted. the nozzle positioned in the eye, the IOL may then be further advanced from the dwell position, in the delivery stage, which may include advancing the IOL through the nozzle and into the eye. However, this multi-step process can be problematic. For example, the user may be required to make a judgement on whether the IOL has been advanced to a proper dwell position in the advancing stage. Thus, the exact position of the IOL in the dwell position can vary from procedure to procedure, which can impact folding of the IOL and integrity of the IOL post-delivery. In addition, multiple actions by the user can increase time in the operation room and, thus, increase cost of the procedure.

SUMMARY

In an exemplary embodiment, the present disclosure is directed to an apparatus for delivery of a lens component into an eye, including: a housing; a nozzle operatively coupled to the housing; a plunger at least partially and moveably disposed within the housing for driving the lens component; and a spring that applies a biasing force to the plunger.

In another exemplary embodiment, the present disclosure is directed to an apparatus for delivery of a lens component into an eye, including: a housing; a nozzle operatively coupled to the housing; a plunger at least partially and moveably disposed within the housing for driving the lens component; a spring that applies a biasing force to the plunger; a retainment structure positioned within the housing that is configured to directly or indirectly engage the spring to retain the spring in a compressed state; and a mechanical stop positioned within the housing to limit forward advance of the plunger after release of the spring from the compressed state.

In another exemplary, the present disclosure is directed to a method for delivery of a lens component into an eye, including releasing a spring from a compressed state causing the spring to extend within a housing thereby moving a plunger within the housing; and displacing the lens component with the plunger.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIGS. 6A and 6B illustrate an insertion tool that is spring-loaded in accordance with some embodiments of the present disclosure.

FIGS. 7A and 7B illustrates another embodiment of an insertion tool that is spring loaded.

DETAILED DESCRIPTION

Figure 1:
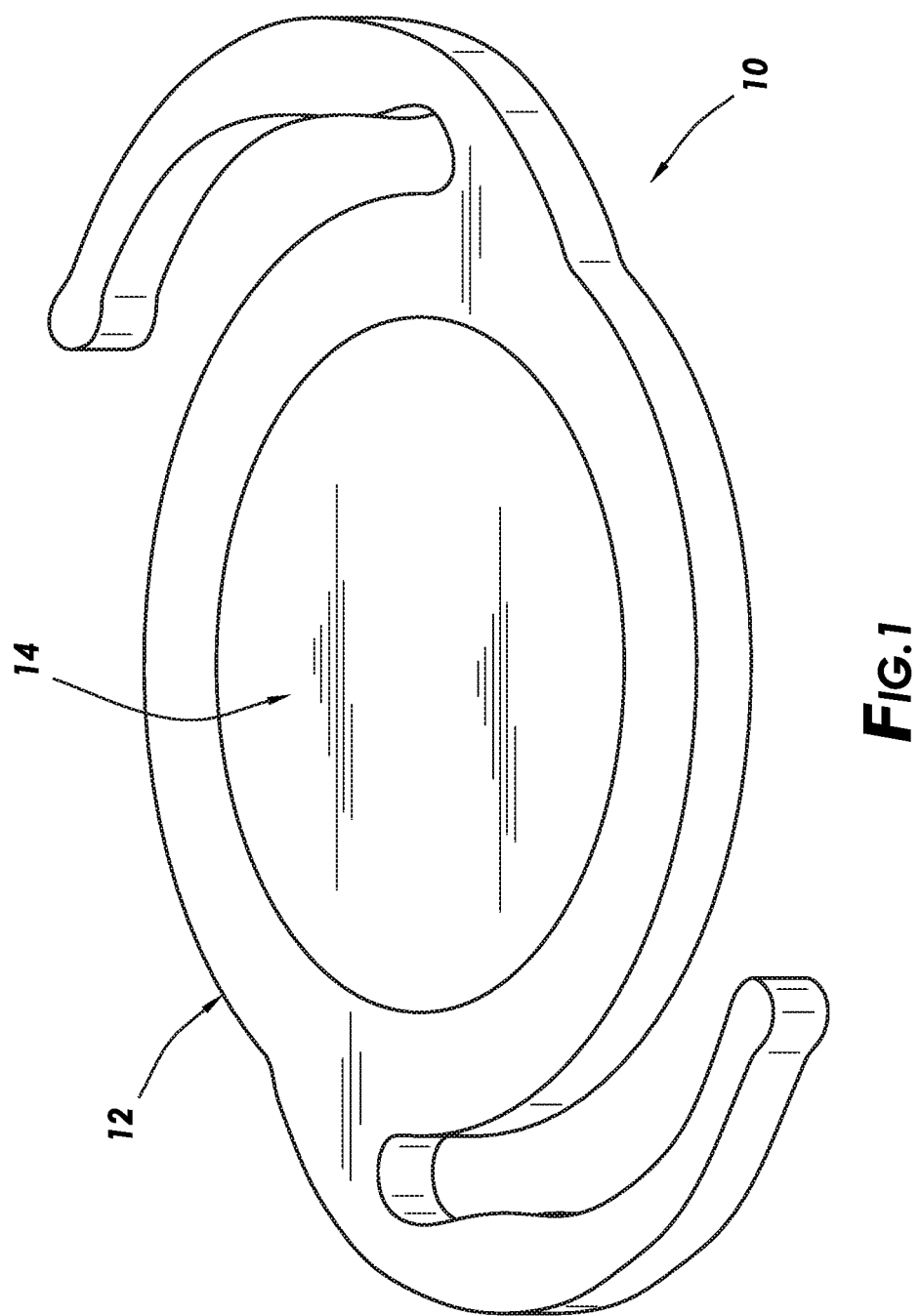
FIG. 1 illustrates a modular IOL with the lens portion positioned in the base portion in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Particular embodiments may generally relate to eye surgery, and, more particularly, may generally relate to systems, methods, and devices for inserting an intraocular lens (IOL). Particular embodiments may include an insertion tool for preparation and delivery of the IOL into a patient's eye that includes a plunger, a nozzle, and a lens holder. In at least one embodiment, the insertion tool may be spring loaded. For example, the insertion tool may include a spring with the spring restrained by a retainment structure. When a user moves the retainment structure, in some embodiments, the spring is released, thereby allowing stored energy in the spring to be delivered to the IOL (or component thereof) by way of the plunger, which engages the IOL. Release of the spring energy should drive the plunger forward to advance the IOL to a predetermined location. For example, the IOL may be advanced from a storage position to a dwell position. At the predetermined location, advance of the IOL may be halted. In some embodiments, the advance may be halted as the spring energy has been consumed. In some embodiments, a mechanical stop may be used to halt advance of the IOL at the predetermined location. At the predetermined location, the IOL (or component thereof) can be in a folded position. The IOL may be folded prior to advancement to the predetermined location or may be folded during this advancement stage. From the predetermined location, the IOL may then be advanced out of the nozzle and into the eye. As will be discussed in more detailed below, any suitable technique may be used for advancement of the IOL during this deployment stage.

Any suitable IOL may be used, including, but not limited to, IOL's that include a lens portion and haptic extensions. The haptic extensions may be side struts (or other suitable extensions) that extend from the lens portion to hold the lens portion in place when implanted in the eye. In at least one embodiment, the IOL may be modular. Particular embodiments of a modular IOL may include a base portion and a lens portion. The base portion may include the haptic extensions. The lens portion may be coupled to the base portion to form the modular IOL.

FIG. 1 illustrates a particular embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
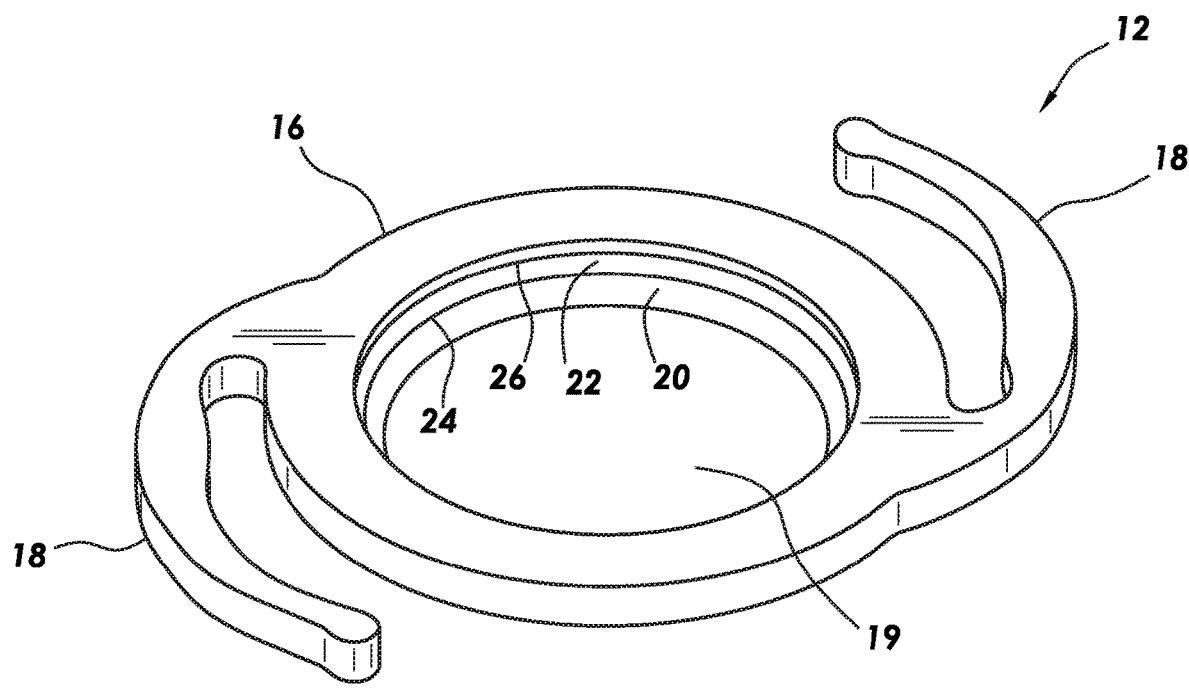
FIG. 2 illustrates a base portion of a modular IOL in accordance with some embodiments of the present disclosure.

FIG. 2 illustrates the base portion 12 of the modular IOL 10 of FIG. 1 in accordance with some embodiments of the present disclosure. In the illustrated embodiment, the base portion 12 includes a base 16 and haptic extensions 18. The haptic extensions 18 may be side struts (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, particular embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding tabs 30 shown on FIG. 3) such that the lens portion 14 can rest inside the hole 19 of the base 16. All or a portion of the lower rim 24 can have an inside diameter that is less than the outside diameter of the lens portion 14 (excluding tabs 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
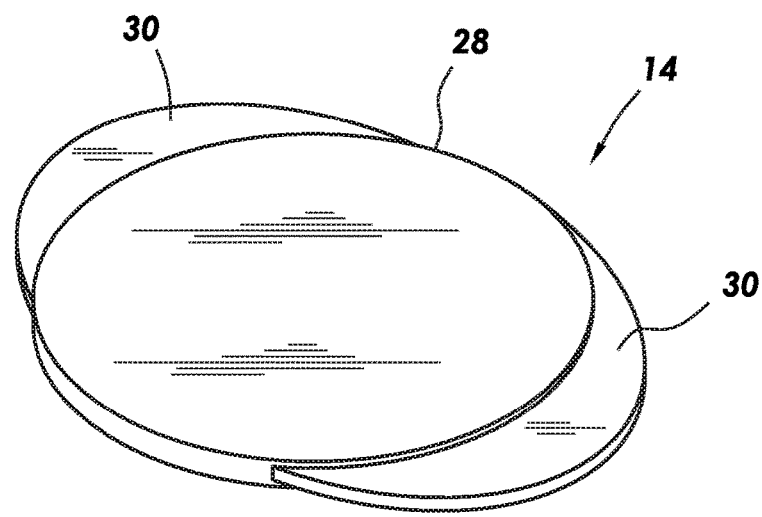
FIG. 3 illustrates a lens portion of a modular IOL in accordance with some embodiments of the present disclosure.

With reference to FIG. 3, the lens portion 14 of the modular IOL 10 of FIG. 1 is illustrated in accordance with some embodiments of the present disclosure. In the illustrated embodiments, the lens portion 14 includes an optic portion 28 and one or more tabs 30. While FIG. 3 illustrates two of the tabs 30, some embodiments may include only one of the tabs 30 or alternatively three, four, or more of the tabs 30. In addition, the tabs 30 on the lens portion 14 may be the same or different from one another. The tabs 30 are shown as being fixed to the optic portion 28; however, it should be understood that one or more of the tabs 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the tabs 30 may have a radius conforming to the inside radius of the recessed groove 22. This arrangement should limit relative movement between the base portion 12 and the lens portion 14 once connected. In some embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the tabs 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

Figure 4:
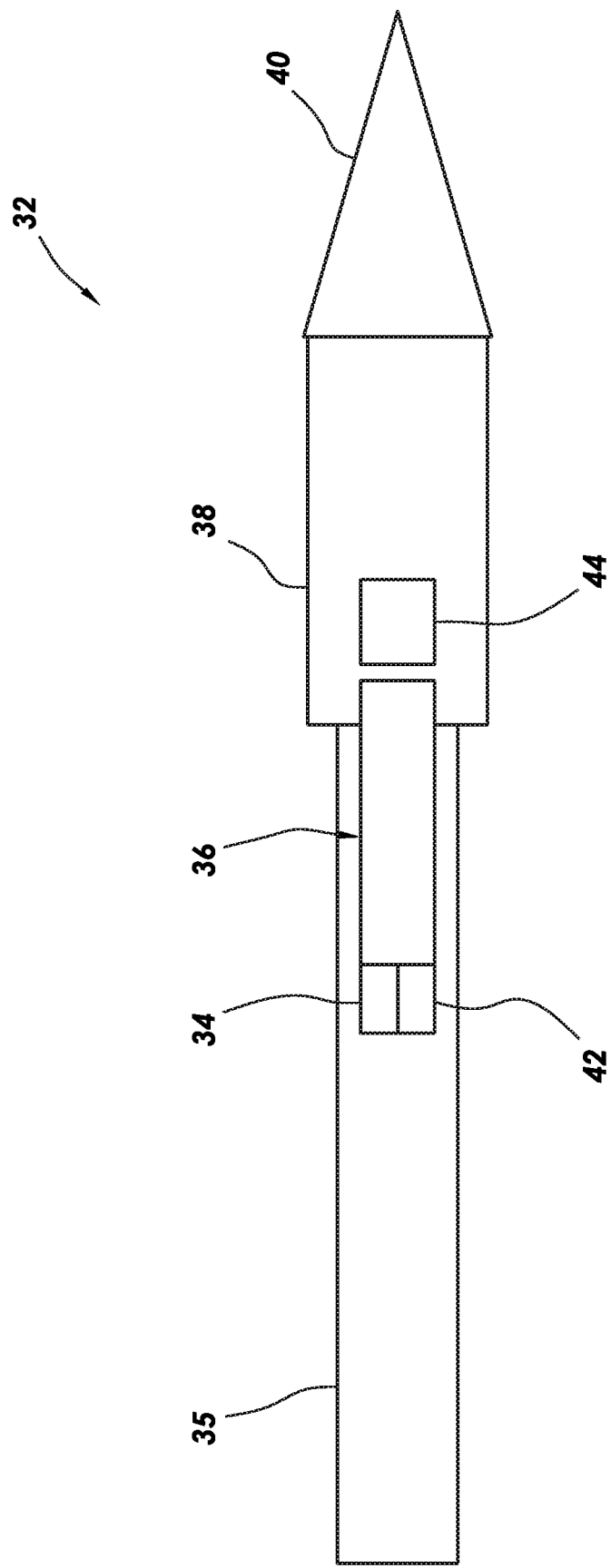
FIG. 4 illustrates an insertion tool in accordance with some embodiments of the present disclosure.

FIG. 4 is a schematic of an insertion tool 32 in accordance with example embodiments. In some embodiments, the insertion tool 32 may include a drive mechanism 34, a plunger 36, a lens holder 38, and a nozzle 40. The plunger 36 may be disposed at least partially in a housing 35. For example, plunger 36 may extend from housing 35 to engage the drive mechanism 34 outside the housing 35. In other embodiments, the plunger 36 may disposed within the housing 35. In some embodiments, the drive mechanism 34 may be operatively coupled to the plunger 36. As illustrated, the plunger 36 may be spring-loaded. For example, the insertion tool 32 may further include a spring 42 that applies a biasing force to the plunger 36. The spring 42 may initially restrained such that the spring 42 has stored potential energy.

The insertion tool 32 may be operable for delivery of a lens component 44 into a patient's eye. The spring 42 may interact with the plunger 36 during the advancement stage for movement of the lens component 44 to a dwell position. The drive mechanism 34 may interact with the lens component during the delivery stage for delivery of the lens component 44 into the eye. The lens component 44 may include any suitable component of an IOL, including the IOL itself or a component of the modular IOL 10 shown on FIG. 2, such as the base portion 12 or the lens portion 14.

In some embodiments, the insertion tool 32 may be preloaded. That is, when provided to an end-user, the insertion tool 32 may have a lens component 44 (e.g., modular IOL 10, base portion 12, or lens portion 14) in an unfolded state already present there within and ready to deliver. Having the insertion tool 32 preloaded with the lens component 44 should reduce the number of steps a user may be required to accomplish before delivering the lens component 44 into a patient. With a reduced number of steps, error and risk associated with delivery of the lens component 44 into a patient may be reduced. Further, an amount of time required to deliver the lens component 44 may also be reduced. In some embodiments, the lens component 44 may be pre-loaded into the lens holder 38.

The drive mechanism 34 may be any suitable combination of components to actuate the plunger 36 for delivery of the lens component into the eye. For example, the drive mechanism 34 may utilize a lever and/or pneumatic systems. The plunger 36 may be operatively coupled to the drive mechanism 34. The drive mechanism 34 may actuate the plunger 36 through any suitable technique including, but not limited to, an electric drive, a mechanical drive, a hydraulic drive, a pneumatic drive, and/or combinations thereof.

As previously described, the plunger 36 may be spring-loaded with the spring 42 applying a biasing force to the spring 42. As illustrated, the spring 42 may be positioned in the insertion tool 32. For example, the spring 42 may be disposed in the housing 35. In at least one embodiment, the spring 42 may be restrained in a compressed configuration such that the spring 42 has stored spring energy. Some embodiments for restraint of the spring 42 in the compressed configuration will be described in more detail below with respect to FIGS. 6A and 6B. The insertion tool 32 may be provided with the spring 42 in a compressed configuration, or a user may compress the spring prior to use to provide stored spring energy. Upon release of the restraint, the spring energy should be released with the spring 42 expanding from its compressed configuration. As the spring 42 expands, the spring 42 should engage the plunger 36 moving the plunger 36 through the insertion tool 32 over a selected distance. In turn, the plunger 36 should engage the lens component 44 advancing the lens component 44 to a predetermined location. For example, the lens component 44 may be advanced from a storage position to a dwell position. Advance of the lens component 44 may be halted at the predetermined location after the plunger 36 has moved the selected distance. Any suitable mechanism may be used for limiting advance of the plunger 36. By way of example, the advance may be halted as the spring energy has been consumed. By way of further example, a mechanical stop (e.g., mechanical stop 84 on FIGS. 7A and 7B) may be used to halt advance of the lens component 44 at the predetermined location. At the predetermined location, the lens component 44 can be in a folded position. The lens component 44 may be folded prior to advancement to the predetermined location or may be folded during this advancement stage. From the predetermined location, the drive mechanism 34 may then be used to advance the lens component 44 out of the nozzle 40 into the eye.

The spring 42 may be any of a variety of suitable spring types suitable for storing spring energy that can be released to move the plunger 36. In general, springs are elastic objects that can stored spring energy. In at least one embodiment, the spring 42 may be designed to operate with a compression load such that the spring 42 stores spring energy upon compression with the spring 42 getting shorter as load is applied. Upon its release, the spring energy should be released causing the spring 42 to extend. Examples of suitable spring types for the spring 42 may include, but are not limited to, coil springs, disc springs, gas springs, and leaf springs, among others. Those of ordinary skill in the art, with the benefit of this disclosure, should be able to determine an appropriate spring type for a particular application.

The plunger 36 may be actuated to move through the lens holder 38. For example, during the advancement stage when driven by spring 42, the plunger 36 may move through the lens holder 38. The lens holder 38 may be disposed at any suitable location within the insertion tool 32, for example, the lens holder 38 may be contained in or inserted into the housing 35 through which the plunger 36 is driven. In some embodiments, the lens holder 38 may be located between the plunger 36 and the nozzle 40. In some embodiments, the lens holder 38 may be a detachable cartridge that may be coupled and decoupled to the housing 35. In other embodiments, the lens holder 38 or one or more features thereof, such as a folding chamber or other surface topography used for folding the lens component may be integrally formed in or a permanent part of the housing 35. In some embodiments, the lens holder 38 may contain a lens component 44. In some embodiments, the lens component 44 may be loaded in the lens holder 38 in an unfolded configuration. The lens holder 38 may be actuated to fold the lens component 44 for delivery the nozzle 40. As used herein, folding of the lens component 44 is also intended to encompass rolling of the lens component 44. For example, the haptic extensions 18 of the base portion 12 shown on FIG. 2 may be folded onto the base 16, which may then be folded or rolled. By way of further example, the lens portion 14 shown on FIG. 2 may be folded or otherwise rolled into a folded configuration for delivery through the nozzle 40. As the plunger 36 moves through the lens holder 38, the plunger 36 may displace the lens component 44 through the nozzle 40.

Figure 5A:
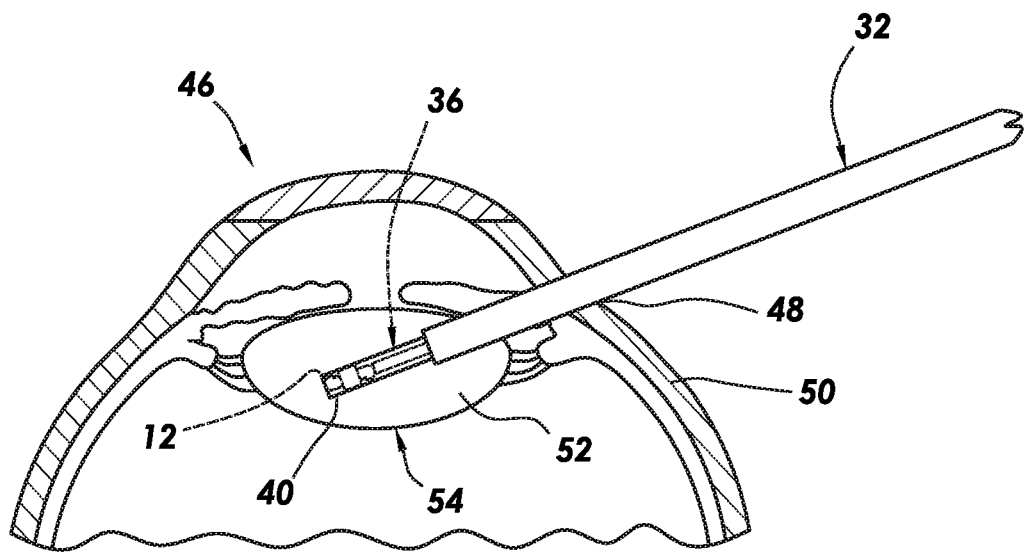
FIGS. 5A-5C illustrate implantation of a modular IOL in accordance with some embodiments of the present disclosure.
Figure 5B:
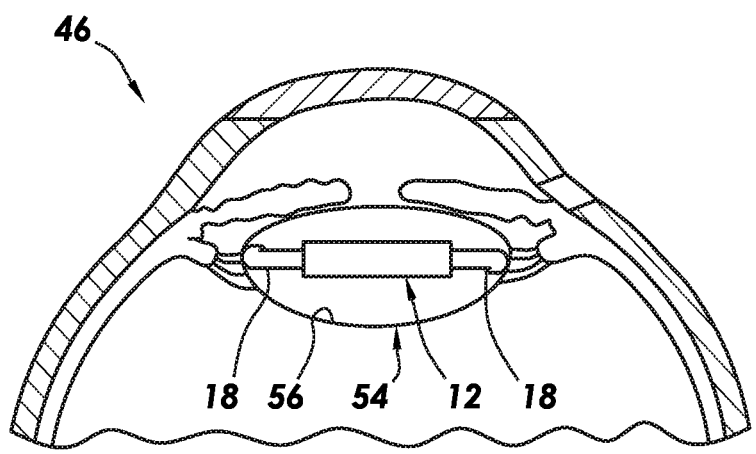

An example technique for implantation of the modular IOL 10 into an eye 46 of a patient will now be described with respect to FIGS. 5A to 5C. As illustrated on FIG. 5A, the insertion tool 32 may first dispense the base portion 12 into the eye 46 of a patient. In some embodiments, an incision 48 may be made in the eye 46 by a surgeon. For example, the incision 48 may be made through the sclera 50 of the eye 46. The incision 48 may be a suitable width or length. In some embodiments, the suitable width and/or length may be less than about 4000 microns (4 millimeters). For example, the incision 48 may have a suitable width and/or length of from about 1000 microns to about 4000 microns, from about 1000 microns to about 3000 microns, or from about 2000 microns to about 3000 microns. After the incision 48 is made, the nozzle 40 of the insertion tool 32 may be inserted through the incision 48 into an interior portion 52 of the eye 46. The insertion tool 32 may be actuated to dispense the base portion 12 into a capsular bag 54 of the eye 46. For example, the spring 42 (e.g., shown on FIG. 4) may first be used to move the base portion 12 a selected distance in the insertion tool 32, for example, from the storage position to the dwell position. This initial movement of the base portion 12 may be performed at any suitable time, for example, before the incision 48 is made. Once the insertion tool 32 is positioned with the nozzle 40 in the eye 46, the insertion tool 32 may then drive the base portion 12 (in a folded (or rolled) configuration) through the nozzle 40 and into the interior portion 52 of the eye 46. Upon dispensation, the base portion 12 should unfurl and settle within the capsular bag 54 of the eye 46, as shown on FIG. 5B. The haptic extensions 18 may be manipulated, for example, to engage the inside equator 56 of the capsular bag 54. The haptic extensions 18 may engage the capsular bag 54 to secure the base portion 12 in the capsular bag 54.

Figure 5C:
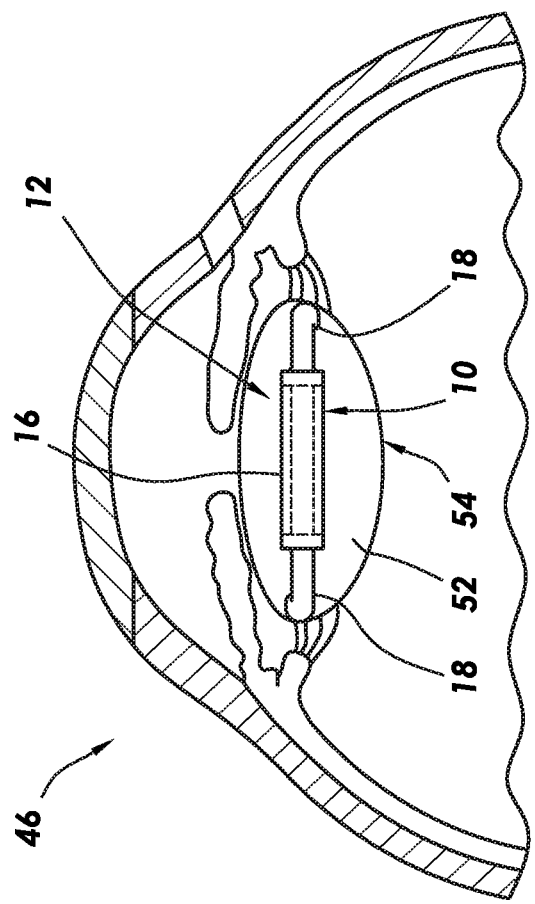

As illustrated on FIG. 5C, the lens portion 14 may be positioned in the interior portion 52 of the eye 46. In the illustrated embodiment, the lens portion 14 is shown positioned in the base 16 of the base portion 12. While not shown on FIG. 5C, the inserter tool 32 shown on FIG. 5A or other suitable inserter may be used for delivery of the lens portion 14 into the eye 46. The lens portion 14 may be delivered in a folded (or rolled configuration) and allowed to unfurl after ejection from the inserter. The lens portion 14 may be positioned in the base 16 of the base portion 12 and secured to the base portion 12, for example, by use of the tabs 30 shown on FIG. 3, to form the modular IOL 10. However, particular embodiments should not be limited to use of the tabs 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 46 so that the lens portion 14 may refract light to be focused on the retina (not shown).

FIGS. 6A and 6B illustrate the insertion tool 32 in accordance with some embodiments of the present disclosure. As illustrated, the insertion tool 32 may be spring-loaded. FIG. 6A illustrates the insertion tool 32 with the spring 42 in a compressed configuration with stored spring energy. FIG. 6B illustrates the insertion tool 32 after release of the spring energy with the lens component in the dwell position 58. The lens component 44 may include any suitable component of an IOL, including the IOL itself or a component of the modular IOL 10 shown on FIG. 2, such as the base portion 12 or the lens portion 14. For simplicity, the drive mechanism 34 used during the advancement stage, for example, is not shown on FIGS. 6A and 6B.

In the illustrated embodiment of FIGS. 6A and 6B, the insertion tool 32 may include the plunger 36, the lens holder 38, the nozzle 40, and the spring 42. Also illustrated is the housing 35 that may house the plunger 36 and the spring 42. The housing 35 may include a proximal portion 60 and a distal portion 62. The distal portion 62 may be configured to receive the lens holder 38. The lens holder 38 may include a lumen 64 that includes a lens chamber 66. In an initial position, the lens component 44 may be positioned in the lens chamber 66, as shown in FIG. 6A, prior to the advancement stage. In at least one embodiment, the lens chamber 66 may include surface features or other topography configured to fold the lens component 44. In other embodiments, the lens component 44 may be folded and then placed into the lens chamber 66. In the advancement stage, the plunger 36 may advance the lens component 44 from the lens chamber 66 to a dwell position 58 in a deployment channel 68 of the nozzle 40, as shown on FIG. 6B. In some embodiments, the lens component 44 may be folded in the advancement stage. While the dwell position 58 is shown in the nozzle 40, the dwell position 58 of the lens component 44 may be otherwise situation, for example, in the lens holder 38, in the distal portion 62 of the housing 35, or in another position in the insertion tool 32. In the deployment stage, the plunger 36 may advance the lens component from the dwell position and out an opening 70 in the nozzle 40.

The nozzle 40 may include a deployment channel 68 that may be aligned with the lumen 64 of the lens holder 38. The deployment channel 68 may receive the lens component 44 from the lens holder 38. The nozzle 40 may further include an opening 70 in a distal tip 72. The opening 70 may provide an exit for the deployment channel 68 so that the lens component 44 can be delivered through the nozzle 40. The housing 35 and/or the lens holder 38 may be configured to receive the nozzle 40. In some embodiments, the nozzle 40 may be attachable the housing 35 and/or the lens holder 38 so that the nozzle 40 can be coupled and decoupled from the housing 35 and/or the lens holder. In other embodiments, the nozzle 40 (or a portion thereof) may be integrally formed in or a permanent part of the housing 35 and/or the lens holder 38.

The plunger 36 may be positioned in the housing 35. The plunger 36 may cooperate with the spring 42 to engage the lens component 44 and push the lens component 44 during the advancement stage. The plunger 36 may include a proximal plunger end 74 and a distal plunger end 76. As illustrated, the distal plunger end 76 may engage the lens component 44. The spring 42 may include a proximal spring end 78 and a distal spring end 80. In at least one embodiment, the spring 42 may be positioned between a backstop 82 and the plunger 36. In some embodiments, the backstop 82 may be proximal wall in the proximal portion 60 of the housing 35. Alternatively, the backstop 82 may be formed on an interior portion of the housing 35. As illustrated, the distal spring end 80 may engage the proximal plunger end 74. It should be understood that the disclosure should not be limited to the configuration of the spring 42 shown on FIGS. 6A and 6B. In some embodiments (not shown), the spring 42 may be otherwise situated, for example, the spring 42 may engage (or otherwise be secured) to another portion of the plunger 36. Additionally, some embodiments may include other spring types other than the coil spring that is shown.

In the illustrated embodiment, the inserter tool 32 may further include a retainment structure 84. The retainment structure 84 may cooperate with the spring 42 to hold the spring 42 in a compressed state so that the spring 42 can store spring energy. The retainment structure 84 may be any suitable structure for holding the spring 42, including, but not limited to, a lockout pin and/or interference fit. As illustrated, the spring 42 may be initially positioned in a compressed state. By way of example, the inserter tool 32 may be provided with the spring 42 in a compressed state or a user may manipulate the inserter tool 32 to compress the spring 42 into a compressed state. The retainment structure 84 can be positioned to hold the spring 42 in the compressed state, as shown on FIG. 6A. As illustrated, the retainment structure 84 can engage a stop 86 at the distal spring end 80 to retain the spring 42. However, it should be understood that the retainment structure 84 can be otherwise configured, for example, the retainment structure 84 can engage the plunger 36, or another component that cooperates with the spring 42, to retain the spring 42 in the compressed state. When desired to release the spring 42, a user can release the retainment structure 84. For example, the user can move the retainment structure 84 from a first position that holds the spring 42 (e.g., FIG. 6A) to a second position that does not hold the spring 42 (e.g., FIG. 6B). In some embodiments, a button, trigger, or other suitable actuating member (not shown) can be provided on the housing 35 that can be manipulated by the user to release the retainment structure 84. When the retainment structure 84 is moved, the spring 42 is released and the stored spring energy may cause the spring 42 to expand from the compressed state of FIG. 6A to an expanded state of FIG. 6B. As the spring 42 expands, the spring 42 should cooperate with the plunger 36 to advance the IOL component 44. For example, the spring 42 should engage the plunger 36 such that the spring 42 and the plunger 36 push the IOL component 44. The IOL component 44 should advance from the lens chamber 66 in the lens holder 38 a selected distance, for example, to the dwell position 58, as shown on FIG. 6B. In some embodiments, the selected distance for advancement may be limited by dissipation of the spring energy and/or a limit on expansion of the spring 42. In other embodiments, the spring 42 may be physically restricted from further advancement. As illustrated, the dwell position 58 may be in a deployment channel 68 formed in the nozzle 40. From the dwell position 58, the lens component 44 may be deployed out through an opening 70 in the nozzle 40. By way of example, a user may actuate the drive mechanism 34 (e.g., shown on FIG. 4) for deployment of the lens component 44 from the nozzle 40.

FIGS. 7A and 7B illustrate an alternative embodiment of the insertion tool 32. As illustrated, the insertion tool 32 that may be spring-loaded with spring 42. FIG. 7A illustrates the insertion tool 32 with the spring 42 in a compressed configuration with stored spring energy. FIG. 7B illustrates the insertion tool 32 after release of the spring energy with the lens component in the dwell position 58. The lens component 44 may include any suitable component of an IOL, including the IOL itself or a component of the modular IOL 10 shown on FIG. 2, such as the base portion 12 or the lens portion 14. For simplicity, the drive mechanism 34 used during the advancement stage, for example, is not shown on FIGS. 6A and 6B.

The particular embodiment of the insertion tool 32 shown on FIGS. 7A and 7B is similar to the example embodiment of FIGS. 6A and 6B. However, the particular embodiment of FIGS. 7A and 7B further includes a mechanical stop 88 that limits forward advancement of the spring 42. The mechanical stop 88 may limit advancement of the spring 42 by any suitable mechanism, for example, by engagement with the spring 42 or by indirect engagement with the spring 42 through engaging the plunger 36 or another component that cooperates with the spring 42. The mechanical stop 88 may be a protrusion from the housing 35, for example, the mechanical stop 88 may be formed on an interior portion of the housing 35. As previously described, the retainment structure 84 may be used to retain the spring 42 in a compressed state, as shown on FIG. 7A. When released, the spring 42 should expand and extend distally in the housing 35. As the spring 42 extends, its distal movement may be restricted by the mechanical stop 88. For example, as the spring 42 moves distally, the spring 42 (or another component such as the plunger 36) may abut the mechanical stop 88, as shown on FIG. 7B, to restrict further expansion of the spring 42. With movement of the spring 42 restricted, the lens component 44 may also be prevented from further distal advancement. In at least one embodiment, the mechanical stop 88 may be positioned, for example, in the housing 35, such that distal movement of the lens component 44 beyond the dwell position 58 is prevented. From the dwell position 58, the lens component 44 may be deployed out through an opening 70 in the nozzle 40. By way of example, a user may actuate the drive mechanism 34 (e.g., shown on FIG. 4) for deployment of the lens component 44 from the nozzle 40.

Use of the methods and systems described herein may provide a number of benefits and advantages over other IOL delivery systems. For example, the inserter tool 32 may be operated to automatically advance the lens component 44 to a selected location in the inserter tool 32 without the user having to perform a separate action. In some embodiments, when the retainment structure 84 is released, the spring 42 should automatically advance the lens component 44 to the dwell position 58. By way of further example, variation in device performance may be reduced as the spring 42 can be used to deliver the lens component to a selected location without additional user interaction. Furthermore, the operation steps may be reduced compared to existing system, thus enabling a user to reduce the overall time associated with inserting the lens component 44, allowing the surgical procedure to be conducted more efficiently and effectively.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of a lens component into an eye, comprising:
 a housing;
 a nozzle operatively coupled to the housing;
 a plunger at least partially and moveably disposed within the housing for driving the lens component;
 a spring that applies a biasing force to the plunger; and
 a retainment structure positioned within the housing that is configured to:
  directly or indirectly engage the spring to retain the spring in a compressed state; and
  release the spring from the compressed state to cause the plunger to move the lens component from a storage position to a dwell position within the nozzle,
 wherein, while the lens component remains at the dwell position within the nozzle, a mechanical stop positioned within the housing limits, without user input, forward movement of the plunger towards the nozzle after release of the spring from the compressed state.

2. The apparatus of claim 1, further comprising an actuating member disposed on the housing that interacts with the retainment structure to move the retainment structure and release the spring from the compressed state.

3. The apparatus of claim 1, wherein the retainment structure engages a stop at an end of the plunger to retain the spring in the compressed state.

4. The apparatus of claim 1, wherein the retainment structure comprises a lockout pin.

5. The apparatus of claim 1, wherein the mechanical stop comprises a protrusion from the housing.

6. The apparatus of claim 1, further comprising a lens holder positionable in the housing with a lumen of the lens holder aligned with a deployment channel of the nozzle, wherein the plunger is positioned to advance through the lumen and the deployment channel when actuated.

7. The apparatus of claim 6, further comprising the lens component positioned in the lens holder.

8. The apparatus of claim 7, wherein the lens component comprises a base portion of a modular intraocular lens or a lens portion of the modular intraocular lens.

9. An apparatus for delivery of a lens component into an eye, comprising:
  a housing;
  a nozzle operatively coupled to the housing;
  a plunger at least partially and moveably disposed within the housing for driving the lens component;
  a spring that applies a biasing force to the plunger;
  a retainment structure positioned within the housing that is configured to:
    directly or indirectly engage the spring to retain the spring in a compressed state; and
    release the spring from the compressed state to cause the plunger to move the lens component from a storage position to a dwell position within the nozzle,
  wherein, while the lens component remains at the dwell position within the nozzle, the spring is in an uncompressed state.

10. The apparatus of claim 9, further comprising an actuating member disposed on the housing that interacts with the retainment structure to move the retainment structure and release the spring from the compressed state.

11. The apparatus of claim 9, wherein the retainment structure engages a stop at an end of the plunger to retain the spring in the compressed state.

12. The apparatus of claim 9, wherein the retainment structure comprises a lockout pin.

13. The apparatus of claim 9, further comprising a lens holder positionable on the housing with a lumen of the lens holder aligned with a deployment channel of the nozzle, wherein the nozzle is positioned to advance through the lumen and the deployment channel when actuated; and further comprises the lens component positioned in the lens holder.

14. The apparatus of claim 9, further comprising a drive mechanism operatively coupled to the plunger and configured to actuate the plunger to advance the lens component from the dwell position to a position outside of the nozzle.

15. The apparatus of claim 14, wherein the drive mechanism is an electric drive, a mechanical drive, a hydraulic drive, a pneumatic drive, or a combination thereof.

* * * * *